US00PP34807P2

(12) United States Plant Patent
Meilland

(10) Patent No.: US PP34,807 P2
(45) Date of Patent: Dec. 13, 2022

(54) MINIATURE ROSE PLANT NAMED 'MEIXOTOK'

(50) Latin Name: *Rosa hybrida*
Varietal Denomination: MEIXOTOK

(71) Applicant: THE CONARD PYLE COMPANY, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 17/565,679

(22) Filed: Dec. 30, 2021

(51) Int. Cl.
*A01H 5/02* (2018.01)
*A01H 6/74* (2018.01)

(52) U.S. Cl.
USPC ..... Plt./116
CPC ..... *A01H 6/749* (2018.05); *A01H 5/02* (2013.01)

(58) Field of Classification Search
USPC ..... Plt./116
CPC ..... A01H 6/749; A01H 5/02
See application file for complete search history.

(56) References Cited

U.S. PATENT DOCUMENTS

PP16,602 P3 5/2006 Lim

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEIXOTOK', is disclosed. The new variety forms attractive, double red-purple colored flowers. Attractive dense with a semi-glossy aspect foliage is formed, which contrasts beautifully with the blossoms. A bushy growth habit is displayed. The new variety is well suited for providing attractive ornamentation in the landscape.

1 Drawing Sheet

Figure 1:
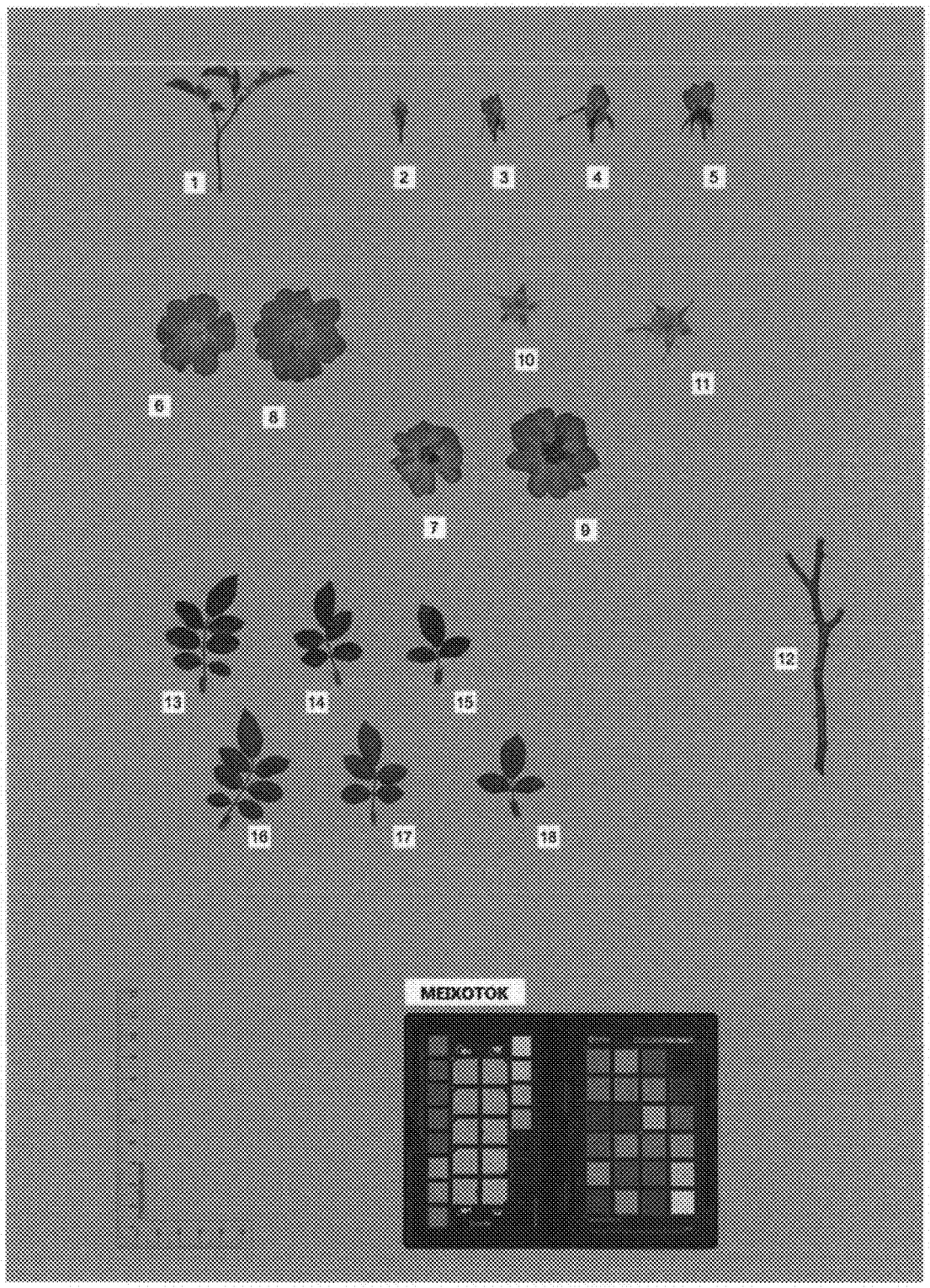

Latin name of genus and species of plant claimed: *Rosa hybrida.*

Variety denomination: 'MEIXOTOK'.

BACKGROUND OF THE INVENTION

The new variety of miniature rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented) from the cross between the 'MEICHANSO' variety (not patented) and the 'ANYTIME' variety (not patented). The male parent (i.e., the pollen parent) of the new variety was the 'BAIPOME' variety (U.S. Plant Pat. No. 16,602).

The parentage of the new variety can be summarized as follows:

('MEICHANSO' x 'ANYTIME') x 'BAIPOME'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) is a very floriferous miniature variety,
(b) forms red purple colored flowers, and
(c) exhibits a semi-glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seed parent ('MEICHANSO' x 'ANYTIME') displays dark red scarlet colored flowers, whereas the new variety displays red purple colored flowers. In addition, the 'BAIPOME' variety (i.e., the pollen parent) displays single type flowers, whereas the new variety displays double type flowers. Moreover, the new variety can be readily distinguished from other similar non-parental varieties. For example, the 'KORVENLANDUS' variety (not patented) displays a ground cover growth habit, whereas the new variety displays a bushy growth habit.

The new variety has been named 'MEIXOTOK'.

The first offer for sale of the new variety was Jan. 28, 2021 in the United States of America by the inventor or another who obtained the new variety directly or indirectly from the inventor.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during April while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—observe.

Element 7—illustrates a specimen of an open flower—plan view—reverse.

Element 8—illustrates a specimen of a fully open flower—plan view—observe.

Element 9—illustrates a specimen of a fully open flower—plan view—reverse.

Element 10—illustrates a specimen of a floral receptacle showing arrangement of the pistils.

Element 11—illustrates a specimen of a floral receptacle showing arrangement of the stamens and pistils (stamens removed).

Element 12—illustrates a specimen of a flowering stem.

Element 13—illustrates a specimen of a leaf with 7 leaflets—plan view—upper surface.

Element 14—illustrates a specimen of a leaf with 5 leaflets—plan view—upper surface.

Element 15—illustrates a specimen of a leaf with 3 leaflets—plan view—upper surface.

Element 16—illustrates a specimen of a leaf with 7 leaflets—plan view—under surface.

Element 17—illustrates a specimen of a leaf with 5 leaflets—plan view—under surface.

Element 18—illustrates a specimen of a leaf with 3 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of one-year-old specimens of the new variety during April while budded on their own roots and growing outdoors at Le Cannet des Maures, Var, France.

Botanical classification: *Rosa hybrida* cultivar MEIXOTOK.

Commercial classification: Miniature Rose Plant.

Plant:

*Habit*.—Bushy.

*Height*.—Typically 30 to 40 cm on average.

*Width*.—Typically 30 to 40 cm on average.

Branches:

*Color*.—Young stems: commonly near Green Group 143A. Adult wood: commonly near a color between Green Group 137A and Green Group 141A.

*Length*.—From the crown to the flower is approximately between 10 to 25 cm on average.

*Diameter*.—Approximately 2.5 mm on average.

*Young shoots*.—Anthocyanin coloration: absent.

*Thorns*.—Configuration on adult stems: slightly concave and elongated on the upper surface and concave on the under surface. Long prickles — Quantity: commonly between 10 to 15 thorns per 10 cm long young stem and commonly between 10 to 15 thorns per 10 cm long adult stem. Long prickles — base shape: narrow obovate. Long prickles — size: approximately 0.3 cm to 0.5 cm in length on average on young stems and on adult stems. Long prickles — color: commonly near Yellow-Green Group 144A more or less suffused with near Greyed-Orange Group 166B on young stems; and commonly near Yellow-Green Group 153A more or less suffused with Greyed-Orange Group 166B at the base of adult stems and near Yellow-Green Group 152A more or less suffused with near Greyed-Orange Group 166B at the top of adult stems. Small prickles — quantity: absent.

*Internode*.—Numbers on the entire branch: commonly between 6 and 9. Length: approximately between 2.0 and 3.5 cm on average.

Foliage:

*General appearance*.—Dense with semi-glossy aspect.

*Number of leaflets*.—3, 5, 7; most often 7.

*Terminal leaflet*.—Length: approximately 3.0 cm on average. Width: approximately 2.0 cm on average.

*New foliage*.—Upper surface color: commonly near a color between Green Group 139A and Green Group 137A. Under surface color: commonly near Green Group 137C. Anthocyanin coloration: absent.

*Adult foliage*.—Upper surface color: commonly near a color between Green Group 139A and Green Group 137A. Under surface color: commonly near Green Group 137C. Anthocyanin coloration: absent.

Leaflets:

*Shape*.—Tip: acuminate. Base: obtuse.

*Glossiness of upper surface*.—Medium.

*Texture*.—Soft.

*General appearance*.—Oblong.

*Serration*.—Small and single.

*Undulation on the margin*.—Weak.

*Venation*.—Color is commonly near Green Group 137A and pattern is imparipinnate.

*Petiole rachis*.—Color of upper surface: commonly near Green Group 137A. Color of under surface: commonly near Yellow-Green Group 144B. Texture: upper surface is smooth, under surface has few prickles. Rachis of terminal leaflet: diameter is approximately 0.1 cm on average.

*Petioles*.—Upper surface: no glandular. Under surface: very few prickles. Color of upper surface: commonly near Green Group 137A at the edge and near Green Group 143A on the center. Color of under surface: commonly near a color between Green Group 143A and Green Group 143B. Length: approximately 2.0 cm on average. Diameter: approximately 0.1 cm on average.

*Stipules*.—General appearance: adnate, pectinate and narrow. Length: approximately 1.0 cm on average. Width: approximately 0.5 cm on average. Color of upper surface: commonly near Green Group 143A edged with near Green Group 137A. Color of under surface: commonly near a color between Green Group 143A and Green Group 143B.

Inflorescence:

*Number of flowers per stem*.—Typically 3 to 5 flowers per stem.

*Lastingness of the bloom*.—On the plant: approximately 10 days on average. In vase: not observed.

*Bud*.—Shape: ovoid. Size: small. Length: approximately 1.5 cm on average. Width: approximately 1.2 cm on average. Color as calyx breaks: upper surface: commonly near Red-Purple Group 57A slightly suffused with near Red Group 53A on the apical part of the petal, basal spot is absent. under surface: commonly near Red-Purple Group 58A, basal spot is absent.

*Sepals*.—Number: commonly 5. Length: approximately 1.6 cm on average. Width: approximately 0.5 cm on average. Shape: at the top: slightly elongated and narrow, at the base: upright. Extensions: commonly 3 sepals have little to medium extensions and the other 2 sepals do not. Upper surface: texture: tomentous. color: commonly near a color between Green Group 139C and Green Group 139D. Under surface: texture: smooth. color: commonly near a color between Green Group 141A and Green Group 141C.

*Receptacle*.—Color: commonly near a color between Green Group 143A and Green Group 143B. Length: approximately 0.7 cm on average. Width: approximately 0.7 cm on average. Surface: smooth. Shape: pitcher shaped.

*Peduncle*.—Length: commonly between 2.5 cm to 4.0 cm. Width: approximately 0.2 cm on average. Surface: slightly glandular. Color: commonly near a color between Green Group 143A and Green Group 143B.

*Flower*.—Diameter when open: approximately 5.0 cm on average. Shape: flat cup shaped. Shape when viewed from above: irregularly round. Profile of the lower part of the flower: flattened convex. Profile of the upper part of the flower: flat. Type: double. Number of petals under normal conditions: typically between 20 to 30 petals on average. Petals: shape at the base: internal petals are acute, and external petals are cuneiform. shape at the top: internal petals are rounded, and external petals are indented. texture: glabrous. length: internal petals are approximately 2.0 cm on average, and external petals are approximately 2.1 cm on average. width: internal petals are approximately 1.0 cm on average, and external petals are approximately 1.8 cm on average. Undulation of the petal: medium. Reflexing of the petal: very weak. Petal incision: weak. Petal arrangement: imbricated without petaloids. Petal drop: petals drop off cleanly before drying. Fragrance: none. Color when opening: basal spot on the upper surface: small, commonly near Yellow-White Group 158B. upper surface: commonly a color gradient near Red-Purple Group 57A from the edge of the petal to Red-Purple Group 57D to the center. basal spot on the under surface: small, commonly near Yellow-White Group 158B. under surface: commonly near Red-Purple Group 57D. Color of the open flower: basal spot on the upper surface: small, commonly near Yellow-White Group 158B. upper surface of the flower: commonly near Red-Purple Group 57C. basal spot on the under surface: small, commonly near Yellow-White Group 158B. under surface of the flower: commonly near Red-Purple Group 74D. Anthers: number is 160 on average, length is approximately 0.5 cm on average, coloration is commonly near Yellow Group 2C edged with Greyed-Orange Group 167A, and arrangement is regular around styles. Filaments: length is approximately 0.1 cm on average and coloration is commonly near Yellow Group 2C. Styles: length is approximately 0.25 cm on average, coloration is commonly near Red-Purple Group 57C, and number is approximately 65 on average. Stigmas: length is approximately 0.1 cm on average, width is approximately 0.1 cm on average, and coloration is commonly near Yellow-Green Group 154C. Pollen: color is commonly near Yellow Group 10C and amount is abundant. Hips: not available at this stage.

Development:

*Vegetation*.—Semi-glossy and strong.

*Blooming*.—Early in the season, very abundant and nearly continuous, typically from May to October in France.

*USDA hardiness zone*.—Zone 5.

*Tolerance to disease*.—Good, and particularly against rust (*Phragmidium tuberculatum*) and Oidium (*Podosphaera pannosa*).

The new 'MEIXOTOK' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIXOTOK' characterized by the following combination of characteristics:

(a) is a very floriferous miniature variety, (b) forms red purple colored flowers, and (c) exhibits a semi-glossy foliage;

substantially as herein shown and described.

* * * * *